(12) United States Patent
Shiber

(10) Patent No.: US 6,440,148 B1
(45) Date of Patent: *Aug. 27, 2002

(54) STENT UNCLOGGING SYSTEM WITH STEPPED SPIRAL

(76) Inventor: Samuel Shiber, 365 Kearney Cir., Manchester, NH (US) 03104

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/643,181

(22) Filed: Aug. 21, 2000

Related U.S. Application Data

(63) Continuation-in-part of application No. 09/286,218, filed on Apr. 5, 1999, now Pat. No. 6,106,538, which is a continuation-in-part of application No. 08/904,972, filed on Aug. 1, 1997, now abandoned, which is a continuation-in-part of application No. 08/516,772, filed on Aug. 18, 1995, now Pat. No. 5,653,696, which is a continuation-in-part of application No. 08/107,453, filed on Aug. 17, 1993, now Pat. No. 5,443,443, which is a continuation-in-part of application No. 07/913,231, filed on Jul. 14, 1992, now Pat. No. 5,334,211, which is a continuation-in-part of application No. 07/662,558, filed on Feb. 28, 1991, now Pat. No. 5,306,244, which is a continuation-in-part of application No. 07/499,726, filed on Mar. 27, 1990, now Pat. No. 5,135,531, which is a continuation-in-part of application No. 07/350,020, filed on May 12, 1989, now Pat. No. 4,979,939, which is a continuation-in-part of application No. 07/326,967, filed on Mar. 22, 1989, now Pat. No. 4,957,482, and a continuation-in-part of application No. 07/324,616, filed on Mar. 16, 1989, now Pat. No. 5,007,896, and a continuation-in-part of application No. 07/323,328, filed on Mar. 13, 1989, now Pat. No. 5,002,553, and a continuation-in-part of application No. 07/332,497, filed on Mar. 13, 1989, now Pat. No. 5,024,651, said application No. 07/326,967, is a continuation-in-part of application No. 07/286,509, filed on Dec. 19, 1988, now Pat. No. 4,894,051, and a continuation-in-part of application No. 07/243,900, filed on Sep. 13, 1988, now Pat. No. 4,886,490, which is a continuation-in-part of application No. 07/225,880, filed on Jul. 29, 1988, now Pat. No. 4,842,579, and a continuation-in-part of application No. 07/205,479, filed on Jun. 13, 1988, now Pat. No. 4,883,458, and a continuation-in-part of application No. 07/078,042, filed on Jul. 27, 1987, now Pat. No. 4,819,634, said application No. 07/324,616, is a continuation-in-part of application No. 07/286,509, and a continuation-in-part of application No. 07/243,900, said application No. 07/323,328, is a continuation-in-part of application No. 07/286,509, and a continuation-in-part of application No. 07/243,900, said application No. 07/332,497, is a continuation-in-part of application No. 07/286,509, and a continuation-in-part of application No. 07/243,900, said application No. 07/225,880, is a continuation-in-part of application No. 07/018,086, filed on Feb. 24, 1987, now Pat. No. 5,041,082, which is a continuation-in-part of application No. 06/874,546, filed on Jun. 16, 1986, now Pat. No. 4,732,154, which is a continuation-in-part of application No. 06/609,846, filed on May 14, 1984, now abandoned, said application No. 07/205,479, is a continuation-in-part of application No. 07/018,086, said application No. 07/078, 042, is a continuation-in-part of application No. 07/018,086.

(51) Int. Cl.[7] ............................................... A61B 17/32
(52) U.S. Cl. ...................................................... 606/159
(58) Field of Search ................................ 606/159, 170, 606/171, 167–184, 185; 604/22

(56) References Cited

U.S. PATENT DOCUMENTS

| | | | | |
|---|---|---|---|---|
| 4,030,503 A | * | 6/1977 | Clark, III | 606/159 |
| 5,078,723 A | * | 1/1992 | Dance et al. | 606/170 |
| 5,423,799 A | * | 6/1995 | Shiu | 606/159 |
| 5,702,412 A | * | 12/1997 | Popov et al. | 606/159 |

\* cited by examiner

Primary Examiner—Kevin T. Truong
(74) Attorney, Agent, or Firm—Samuel Shiber

(57) ABSTRACT

An atherectomy system for removing obstructive material from within a patient's vessel comprising a flexible spiral wire having a distal stepped-down section that is connected through a short transition section with a nominal diameter section, a flexible catheter that is slideable and rotateable over the spiral wire and rotating means coupled to the catheter.

1 Claim, 1 Drawing Sheet

STENT UNCLOGGING SYSTEM WITH STEPPED SPIRAL

CROSS REFERENCE TO OTHER APPLICATIONS

This application is a continuation in part (CIP) of application Ser. No. 09/286,218 filed Apr. 5, 1999 (CT19 now U.S. Pat. No. 6,106,538) which is a CIP of application Ser. No. 08/904,972 filed Aug. 11, 1997 (CT18 abandoned) which is a CIP of application Ser. No. 08/516,772 filed Aug. 18, 1995 (CT17 now U.S. Pat. No. 5,653,696) which is a CIP of application Ser. No. 08/107,453 filed Aug. 17, 1993 (CT16 now U.S. Pat. No. 5,443,443) which is a CIP of application Ser. No. 07/913,231 filed Jul. 14, 1992 (CT15 now U.S. Pat. No. 5,334,211) which is a CIP of application Ser. No. 07/662,558 filed Feb. 28, 1991 (CT14 now U.S. Pat. No. 5,306,244) which is a CIP of application Ser. No. 07/499,726 filed Mar. 27, 1990 (CT13 now U.S. Pat. No. 5,135,531) which is a CIP of application Ser. No. 07/350,020 filed May 12, 1989 (CT12 now U.S. Pat. No. 4,979,939) which is a CIP of four applications: application Ser. No. 07/326,967 filed Mar. 22, 1989 (CT11 now U.S. Pat. No. 4,957,482), application Ser. No. 07/324,616 filed Mar. 16, 1989 (CT10 now U.S. Pat. No. 5,007,896), application Ser. No. 07/323,328 filed Mar. 13, 1989 (CT9 now U.S. Pat. No. 5,002,553) and application Ser. No. 07/332,497 filed Mar. 13, 1989 (CT8 now U.S. Pat. No. 5,024,651).

These four applications are CIPs of application Ser. No. 07/286,509 filed Dec. 19, 1988 (CT7 now U.S. Pat. No. 4,894,051) which is a CIP of application Ser. No. 07/243,900 filed Sep. 13, 1988 (CT6 now U.S. Pat. No. 4,886,490), which is a CIP of three applications: application Ser. No. 07/225,880 filed Jul. 29, 1988 (CT5 now U.S. Pat. No. 4,842,579) including Reexamination Request 90/003,608 filed Oct. 19, 1994 (now Reexamination Certificate 2711th issued on Oct. 31, 1995), application Ser. No. 07/205,479 filed Jun. 13, 1988 (CT4 now U.S. Pat. No. 4,883,458), and application Ser. No. 07/078,042 filed Jul. 27, 1987 (CT3 now U.S. Pat. No. 4,819,634).

These three applications are CIPs of application Ser. No. 07/018,083 filed Feb. 24, 1987 (CT2 now U.S. Pat. No. 5,041,082) which is a CIP of application Ser. No. 06/874,546 filed Jun. 16, 1986 (CT1 now U.S. Pat. No. 4,732,154) which is a CIP of application Ser. No. 06/609,846 filed May 14, 1984 (CT0 now abandoned).

All the above applications are being incorporated herein by reference.

BACKGROUND AND OBJECTIVES OF THE INVENTION

With age, a large percentage of the population develops atherosclerotic arterial obstructions resulting in diminished blood circulation. The disturbance to the blood flow that these obstructions cause may induce blood clots which further diminish or block the blood flow. When this process occurs in the coronary arteries it is referred to as a "heart attack". Presently such obstructions are circumvented surgically by grafting a bypass, or they are treated by a catheter equipped with a balloon which is inserted through the arterial system, over a flexible guide wire assembly, into the obstruction and then inflated to expand the obstruction's lumen, a procedure known as angioplasty.

Angioplasty, which breaks up but does not remove the obstructive material out of the arterial system, creates an irregular lumen which tends to partially recoil after the balloon is deflated and withdrawn. To lessen this phenomena a stent may be placed in the blood vessel to provide support (further information on Intravascular stents is available in chapter 56 of the 2nd edition of a book titled *Endovascular Surgery* by Samuel S. Ahn and Wesley S. Moore, which was published in 1992 by W. B. Saunders Co. which is hereby incorporated by reference).

Stents may also be useful in other vessels of the human anatomy, therefore, the term "vessel" as used hereinafter shall mean a tubular fluid conduit in the body such as blood vessels and biliary ducts. For example, stents may be inserted in narrowed biliary ducts to keep these ducts open for bile drainage (further information on biliary stents is available in chapter 7 of the 3rd edition of a book titled *Practical Gastrointestinal Endoscopy* by Peter B. Cotton and Christopher B., Williams, which was published by Blackwell Scientific Publications which is hereby incorporated by reference).

The stent itself, however, may become obstructed. An objective of the present invention is to provide a stent unclogging method and hardware for reopening and cleaning obstructed stents.

These and other objectives of the invention will become apparent from the following discussion and the accompanying drawing.

DETAILED DESCRIPTION OF THE DRAWING

Figure 1:
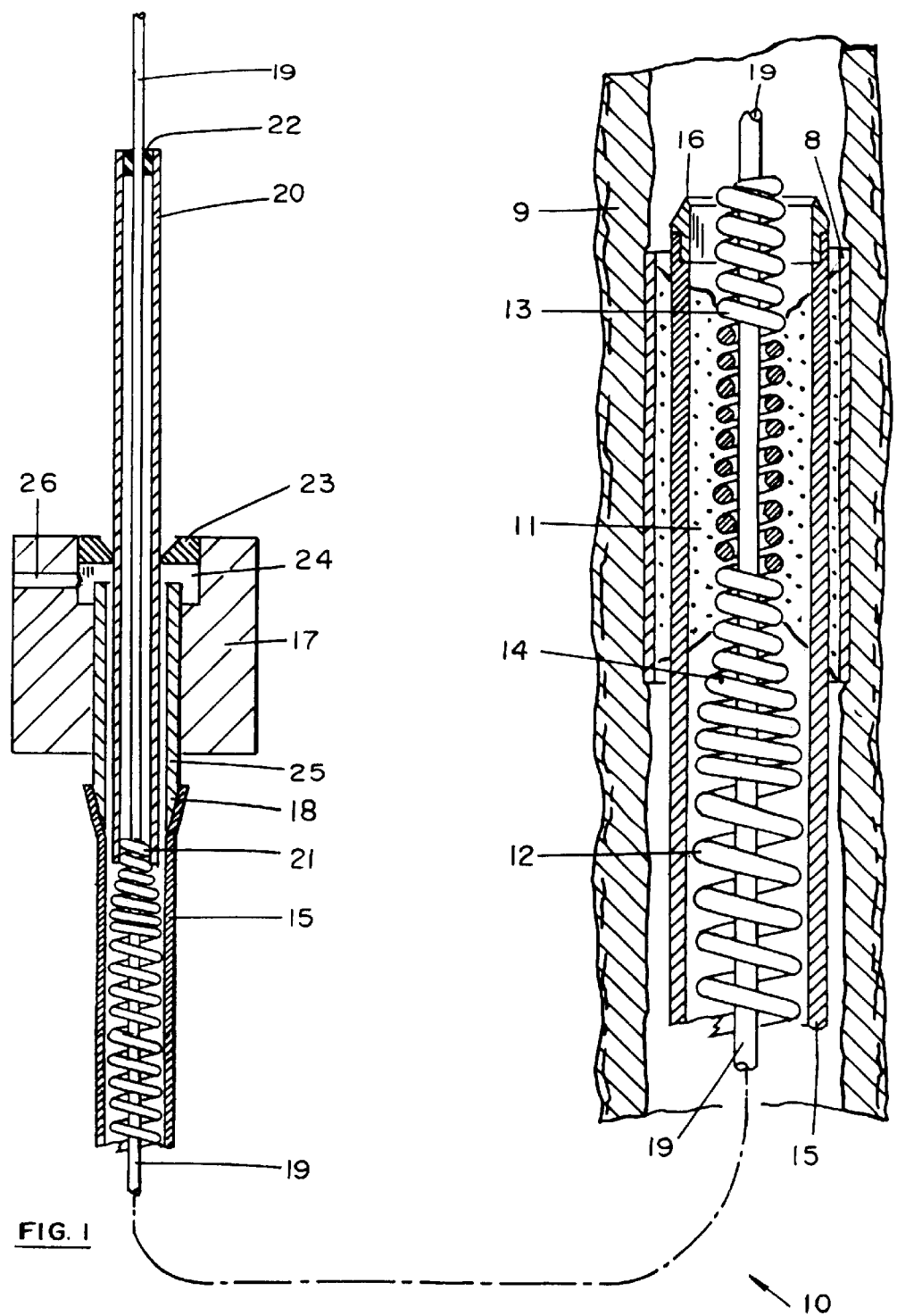
FIG. 1 shows a stent unclogging system according to the present invention.

FIG. 1 shows a stent unclogging system 10, for removing obstructive material 11 from within a stent 8 located in a patients vessel 9. One major component of the system is a flexible spiral wire having a distal stepped-down section 13 that is connected through a short transition section 14 with a nominal diameter section 12. As illustrated in FIG. 1 the stepped-down section has a smaller diameter than the nominal diameter, and the transition section has a nominal diameter at one end and a stepped down diameter at the other end.

A second major component of the system is a flexible catheter 15 that is slideable and rotateable over the spiral wire and has a tubular blade 16 affixed at its distal end. A motor 17 (e.g., a motor driven by electricity or compressed gas) serves as a rotating means and has an output-shaft with a conical end 18 that seals and couples the motor to the catheter.

The flexible spiral wire is slideable over a guidewire 19 and is equipped with a handle 20 made of a tube section that is attached to a short transition section 21 at the proximal end of the flexible spiral wire. A first seal 22 that is disposed between the handle and the guidewire seals the catheter.

A second seal 23 that is disposed between the motor and the handle allows the handle to slide and rotate through it while defining a sealed cavity 24. Cavity 24 connects, through a motors hollow shaft 25, to the catheter 15 on one side and to a fluid port 26 on the other side allowing the introduction of fluids, or negative pressure, through the catheter.

Operation

Unclogging a stent that is located in a patient's vessel can be done as follows:

Threading the guidewire through the vessel and advancing it to the vicinity of, or preferably through the stent, as shown in FIG. 1.

Threading the stepped-down section 13 into the obstructive material 11 until the transition section 14 is advanced to the vicinity of the proximal end of the stent. It can be appreciated, the larger diameter coils of the spiral provide closer guidance for the blade at its entry point into the stent whereas the smaller coils of the stepped down section are less likely to interfere with the blade's advancement through the stent.

Passing the preferably rotating tubular catheter and blade 16 over the flexible spiral wire and the obstructive material 11 thereby separating the bulk of the obstructive material from the stent 8, and then withdrawing the spiral wire and catheter that contain the obstructive material out of the stent and further out of the patient's body.

While the present invention has been illustrated by a limited number of examples, it should be understood that various modifications and substitutions may be made in the apparatus and method of its use without departing from the spirit of the invention or the scope of the claims.

I claim:

1. A method for unclogging a stent that is located in a patient's vessel, with a catheter system that has a flexible spiral wire having a distal stepped-down section, and a flexible catheter that is slideable and rotateable over the spiral wire, said catheter having a tubular blade at its distal end and rotating means coupled to the catheter, said method comprising the following steps;

threading a guidewire through the vessel and advancing it to the vicinity of the stent, threading said distal stepped-down section into an obstructive material that is clogging the stent, passing a tubular blade over the flexible spiral wire and the obstructive material thereby separating the obstructive material from the stent, and withdrawing the spiral wire and the tubular blade with the obstructive material out of the stent.

\* \* \* \* \*